(12) United States Patent
Liu (10) Patent No.: US 6,553,281 B1
(45) Date of Patent: Apr. 22, 2003

(54) DEVICE FOR DETERMINING A FIXATION POINT

(75) Inventor: Jin Liu, Berlin (DE)

(73) Assignee: Heinrich-Hertz-Institut fuer Nachrichtentechnik Berlin GmbH, Berlin (DE)

(*) Notice: Subject to any disclaimer, the term of this patent is extended or adjusted under 35 U.S.C. 154(b) by 0 days.

(21) Appl. No.: 09/486,584

(22) PCT Filed: Aug. 26, 1998

(86) PCT No.: PCT/DE98/02580

§ 371 (c)(1),
(2), (4) Date: Feb. 28, 2000

(87) PCT Pub. No.: WO99/09880

PCT Pub. Date: Mar. 4, 1999

(30) Foreign Application Priority Data

Aug. 26, 1997 (DE) .......................................... 197 36 995

(51) Int. Cl.[7] ................................................. G05D 1/02
(52) U.S. Cl. ...................................... 700/302; 351/210
(58) Field of Search ................................. 700/302, 275, 700/56, 57, 59, 60, 61, 62, 66; 351/209, 210, 205, 246

(56) References Cited

U.S. PATENT DOCUMENTS

| 4,582,403 A | | 4/1986 | Weinblatt | |
| 4,613,219 A | * | 9/1986 | Vogel | 351/210 |
| 4,755,045 A | * | 7/1988 | Borah et al. | 351/210 |
| 4,789,235 A | * | 12/1988 | Borah et al. | 351/210 |
| 4,859,050 A | * | 8/1989 | Borah et al. | 351/210 |
| 5,587,748 A | * | 12/1996 | Luce et al. | 351/209 |
| 6,367,932 B1 | * | 4/2002 | Donaldson | 351/237 |

OTHER PUBLICATIONS

EP 0 631 222 A (IBM) Dec. 28, 1994.*

* cited by examiner

Primary Examiner—Ramesh Patel
Assistant Examiner—Edward F. Gain
(74) Attorney, Agent, or Firm—Karl Hormann (57) ABSTRACT

The invention relates to a device for determining a fixation point (3) on screen (1), comprising an eye reference point detector (6) an a direction of view detector (9) which is mounted on a pivoting/inclining element (11) in such a way that it can be pivoted and inclined. By means of three transformation steps, namely rotation, scaling and translation, a direction of view function can be transformed by a system of direction of view coordinates assigned to the direction of view detector (9) in an object coordinate system which is assigned to the screen (1). In this way it is possible, to trigger certain functions by fixation of areas of the screen (1) rendered sensitive, whereby the eye plays the role of a mouse.

6 Claims, 6 Drawing Sheets

DEVICE FOR DETERMINING A FIXATION POINT

BACKGROUND OF THE INVENTION

The invention relates to an apparatus for estimating a fixation point of an anthropomorphically constructed eye when gazing at an object with an eye reference point detection device with which eye reference point coordinate values of an eye reference point may be defined, with a direction of gaze detection device with which a gazing direction of the eye may be defined as a gaze direction function, and with a computer with which the fixation point of the eye may be estimated on the basis of the gaze direction function and the eye reference point coordinate values.

Such an apparatus is known from appendix 2the prior art of the final report of the project "Fernseh-Bildgüte bei dynamischem Blickverhalten" (Television Image Quality at Dynamic Viewing Behavior) sponsored under Sponger reference 01BK203/8 by the (German) Federal Ministry for Education, Science, Research and Technology. In the known apparatus, a rigidly mounted head position transmitter and a head position detector arranged, for instance, on a spectacle-like frame on the head of a subject are provided as an eye reference point detection device. Furthermore, the apparatus is provided with a computer for calculating the position of the head position detector relative to the head position transmitter as spatial coordinates, i.e. the distance and bearing of the head position detector with respect to the head position transmitter.

In addition, the known apparatus is provided with a gaze direction detection device which is also mounted on the frame and which is equipped for detecting a gaze directional function of an eye the fixation point of which is to be monitored on an viewing screen. In this context, the gaze direction function is derived by a method of calibration from the known fact that the position of the eye detected by two measurement values may be unambiguously assigned to a gaze direction function. Furthermore, in the prior art device a translation vector between the head position detector and an eye reference point, for instance, the center of the pupil or the center of the eye, is determined by estimation.

For estimating a fixation point on the viewing screen, the gaze direction function is scaled by the computer by relatively complex calculations, shifted by the translation vector, multiplied by a rotary matrix representing the bearing of the head relative to the head position transmitter, and corrected by the vector of the distance between the head position transmitter and the head position detector. For calculating the scaling factor, the rotary matrix representing the bearing of the head is multiplied, on the one hand, by the vector of translation between the head position detector and the eye reference point and, on the other hand, by the vectorial gaze direction function, followed by quotient formation. The two results of the multiplication are divided by one another.

A similarly constructed apparatus with a frame to be mounted to a head and supporting a head position sensor, an eye reference point detection and a gaze direction detection device, is known from the article "Gaze Point Direction System Allowing Head Motion" by M. Lida and A. Tomono in Systems and Computers in Japan, Vol. 23, No. 6, 1992.

From U.S. Pat. No. 4,582,403, there is known an apparatus by which head movement may be compensated when determining a fixation point, by monitoring a reference point by reference point monitoring means. This apparatus is structured, in one embodiment, as an uncomfortable—for the subject—eyeglass frame which supports a reference point detector for monitoring a reference point on an image screen as well as a device for detecting the gaze direction. In another embodiment, the reference point to be monitored is applied, for instance, to the forehead of the subject as a spot of a layer which is highly reflective in the infrared spectral range. This, however, may entail the risk of the reference point becoming separated, so that the apparatus would have to be completely calibrated again.

OBJECT OF THE INVENTION

The task of the invention resides in the provision of an apparatus of the king mentioned above which makes it possible to monitor a fixation point on an object to be viewed quickly and without in the least disturbing the subject.

SUMMARY OF THE INVENTION

In an apparatus of the kind referred to above, this task is accomplished in accordance with the invention by the eye reference point detection device comprising a reference point detector structured as a surface detector by means of which an image of the eye may be formed within a predetermined spatial area, by the gaze direction detection device comprising a gaze direction detector structured as a surface detector which is mounted on a pivoting and tilting element which is pivotable and tiltable in two overlapping directions, whereby an image may be formed by the gaze direction detector at least of the pupil and the immediate surroundings of the pupil and whereby the pivoting and tilting element may be adjusted by a tracking unit fed by control signals from the eye reference point detection device such that upon spatial movement of the eye reference point the gaze direction detector remains aligned with the eye reference point, and by the computer comprising a compensation unit for the compensation of movement of the eye reference point which compensation unit may be fed with object coordination values associated to the object, gaze direction detector coordinate values associated with the gaze direction detector, gaze direction values associated in a gaze direction coordinate system to the gaze direction function, alignment values associated with the alignment of the gaze direction detector and eye reference point coordinate values for estimating (determining) the fixation point.

In view of the fact that for estimating the fixation point only the eye of a subject is optically monitored without being touched and that head movements are compensated for by the compensation unit by calculations of the data fed to the compensation unit and derived from the eye reference point detector and the gaze direction detector as well as the pivoting and tilting element the fixation point may be determined with relatively low mathematical complexity by executing mathematical rotation, scaling and translation steps, which in a preferred embodiment of the invention may be executed by a rotation compensation member, a scaling member and a translation compensation member.

For a highly precise monitoring of the eye reference point, the eye reference point detection device as well as the gaze direction detector are each equipped with a surface camera acting as a surface detector. To this end, the surface camera of the eye reference point detection device preferably monitors the head portion of the subject without a spatial area in which movements may be expected, whereas the surface camera of the gaze direction detection device monitors the immediate vicinity of the pupil of the eye at high resolution.

In a further embodiment the eye reference point detection device and the gaze direction detection device are provided with a common surface camera as a dual detector of high resolution, the camera being structured as an autofocus camera the autofocus positions of which may be fed to the calculator for determining the distance of the eye reference point which is preferably been derived from the pupil of the eye, from the detector plane of the dual detector. In this manner, the expenditure in terms of equipment is relatively low.

DESCRIPTION OF THE SEVERAL DRAWINGS

Further efficacious arrangements and advantages of the invention have been defined in the sub-claims as well as in the ensuing description of embodiments of the invention. In the drawings:

DETAILED DESCRIPTION OF THE PREFERRED EMBODIMENTS

Figure 1:
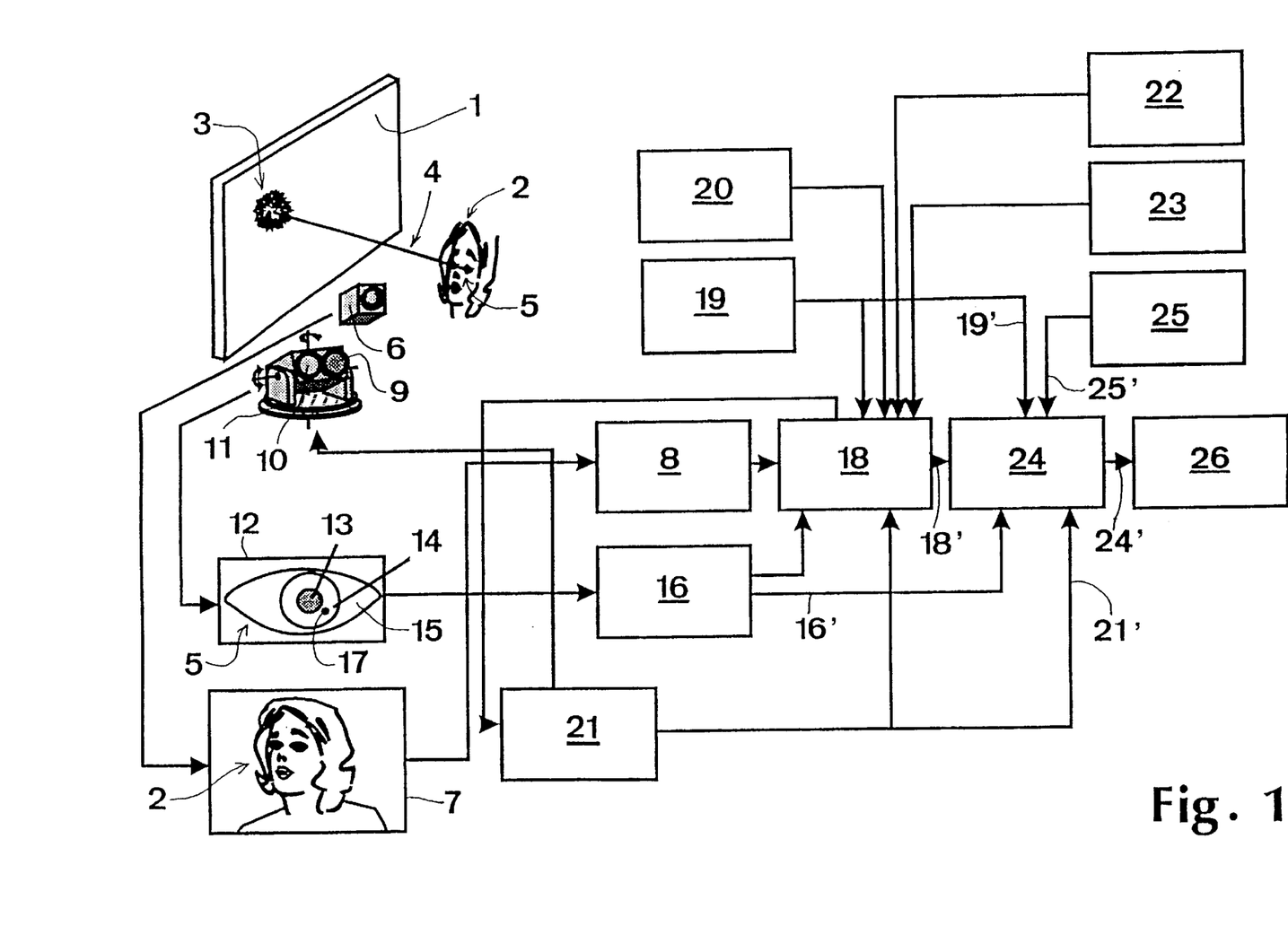
FIG. 1 is a block diagram of an embodiment of the apparatus in accordance with the invention in which an eye reference point detection device and a gaze direction detection device are each equipped with a surface detector.

FIG. 1 is a block diagram depicting an embodiment of an apparatus for estimating (determining) a fixation point in accordance with the invention. To estimate a fixation point 3 of an object viewed by a person 2 on an image screen 1 of a work station computer, the fixation point 3 being understood to be the point on the image screen 1 impinged by the gaze line 4 of an eye 5 of the person 2, there is provided an eye reference point detection device equipped with an eye reference point detector 6. The eye reference point detector 6 is formed, for instance, by a video camera of short focal length functioning as a surface detector. By means of the eye reference point detector 6 it is possible, within a predetermined spatial range, to monitor, and store as image data in a head image storage 7, for instance the head and shoulder portion of the person 2. The head image storage 7 is connected to a surface eye reference point determining unit 8 of the eye reference point detection device which serves to define an eye reference point from the image data of the head image storage 7. For reasons of measurement technology the eye reference point preferably is the center of the pupil.

The device of FIG. 1 is additionally provided with a gaze direction detector 9 structured, for instance, as a long focal length video camera functioning as a surface detector and which is mounted, together with a source of illumination 10, as a pivot and tilt element, on a pivot and tilt platform 11 which is pivotable and tiltable in two dimensions. The source of illumination 10 is structured, for instance, as an array of light emitting diodes emitting, for instance, in the near infrared spectral range, for instance at about 880 nanometers, the radiation of which is directed in the same direction as a viewing range of the gaze direction detector 9. The gaze direction detector 9 is equipped with an autofocus module which makes it possible to form a sharply focused image of the eye 5 even at a change of the distance between the eye 5 and the gaze direction detector 9. The gaze direction detector 9 is aimed at the eye 5 of the person 2 the fixation point 3 of which is to be estimated. With the embodiment of FIG. 1 it is possible to monitor the eye 5 with its pupil, the cornea and the visible portion of the sclera.

The gaze direction detector 9 is connected to an eye image storage 12 where its image data may be stored. In the presentation of FIG. 1, there is schematically depicted, as storable image data, an image of the eye 5 with its pupil 13 and its surrounding iris 14 and the visible portion of the sclera 15. The eye image storage 12 is connected to a surface gaze direction determining unit 16 of the gaze direction determination device with which it is possible unambiguously to calculate a gaze direction function on the basis of the known cornea reflex method. The calculation is based on measurement values derived from the monotonal connection between a reflex center 17 detected by irradiation with the light output from the source of illumination 10 on the cornea of the eye 5 and the center of the pupil 13, after execution of a calibration process. Furthermore, the surface-related two-dimensional coordinates of the eye reference point in the detector plane of the gaze direction detector 9 may be determined by the surface gaze direction determination unit 16 in a gaze direction detector coordinate system associated with the gaze direction detector 9.

The eye reference point detection device of the apparatus of FIG. 1 is provided with a spatial eye reference point determining unit 18 connected to the surface eye reference point determination unit 8. The spatial eye reference point determination unit 18 is connected to the surface gaze direction determination unit 16 and may be fed with the eye reference point coordinate values in the gaze direction coordinate system. Furthermore, the spatial eye reference point determination unit 18 may be fed with original spatial coordinates as gaze direction detector coordinate values from a gaze direction detector coordinate storage 19, the original spatial coordinates representing the origin of the gaze direction coordinate system.

The spatial eye reference point determination unit 18 may be fed with parametric data from a gaze direction detector parameter storage 20 having associated therewith imaging characteristics of the gaze direction detector 9. Finally, the spatial eye reference point detection unit 18 may be fed, from a tracking unit 21, with a pivot angle value and a tilt angle value for controlling, by means of related adjustment signals, adjustment elements of the pivot and tilt platform 11 for aligning the gaze direction detector 9 and the source of illumination 10 with the eye 5 of the person 2.

Furthermore, an eye reference point detector parameter storage 22 and an eye reference point detector coordinate storage 23 are connected to the spatial eye reference point determination unit 18 to which may be fed device parameters of the eye reference point detector 6 and origin coordinate values of an aye reference point detector coordinate system associated with the eye reference point detector 6 for calculating eye reference point coordinate values.

Spatial eye reference point coordinate values in the gaze direction coordinate system as well as in a display coordinate system associated with the image screen 1 may be calculated by the spatial eye reference point determination unit 18. The eye reference point coordinate values in the gaze direction coordinate system may be fed back to the tracking unit 21 through a feed-back line and serve for determining of new tilt angle values and pivot angle values for the tracking alignment of the gaze direction detector 9 with the eye 5.

Eye reference point coordinate values in the display coordinate system may be fed through a spatial eye reference point line 18' to an eye reference point movement compensation unit 24 of a computer connected to the spatial eye reference point determination unit 18. The eye reference point movement compensation unit 24 is also connected to the surface gaze direction determination unit 16 through a gaze direction line 16', to a gaze direction detector coordinate storage 19 through a gaze direction detector coordinate line 19', to the tracking unit 21 through a tracking unit line 21' as well as to an image screen coordinate storage 25 through an image screen coordinate line 25'. By means of the surface gaze direction determination unit 16, gaze direction function values in the gaze direction coordinate system may be fed to the eye reference point movement compensation unit 24. From the tracking unit 21, the pivot angle values and the tilt angle values of the gaze direction detector 9 may be fed to the eye reference point movement compensation unit 24.

Finally, the origin coordinate values for the gaze direction sensor 9 in the associated gaze direction coordinate system may be fed to the eye reference point movement compensation unit 24 from the gaze direction detector coordinate storage 19. Also, the spatial coordinate values of the image screen 1 may be fed to the eye reference point movement compensation unit 24 as subject coordinate values from the image screen coordinate storage 25. As will be explained in greater detail hereinafter, the gaze direction function values in the gaze direction coordinate system may be transformed into fixation point coordinate values of the fixation point 3 in the display coordinate system by compensation of, for instance, spatial changes in the eye reference point, and fed through a fixation point line 24' to a fixation point coordinate evaluation unit 26 at the output of the eye reference point compensation unit 24. Switching functions for controlling the work station computer provided with the image screen 1 may be initiated by the fixation point coordinate evaluation unit 26 if the fixation point 3 coincides with, and remains for a predetermined time in, window sections symbolically representing predetermined switching functions.

Figure 2:
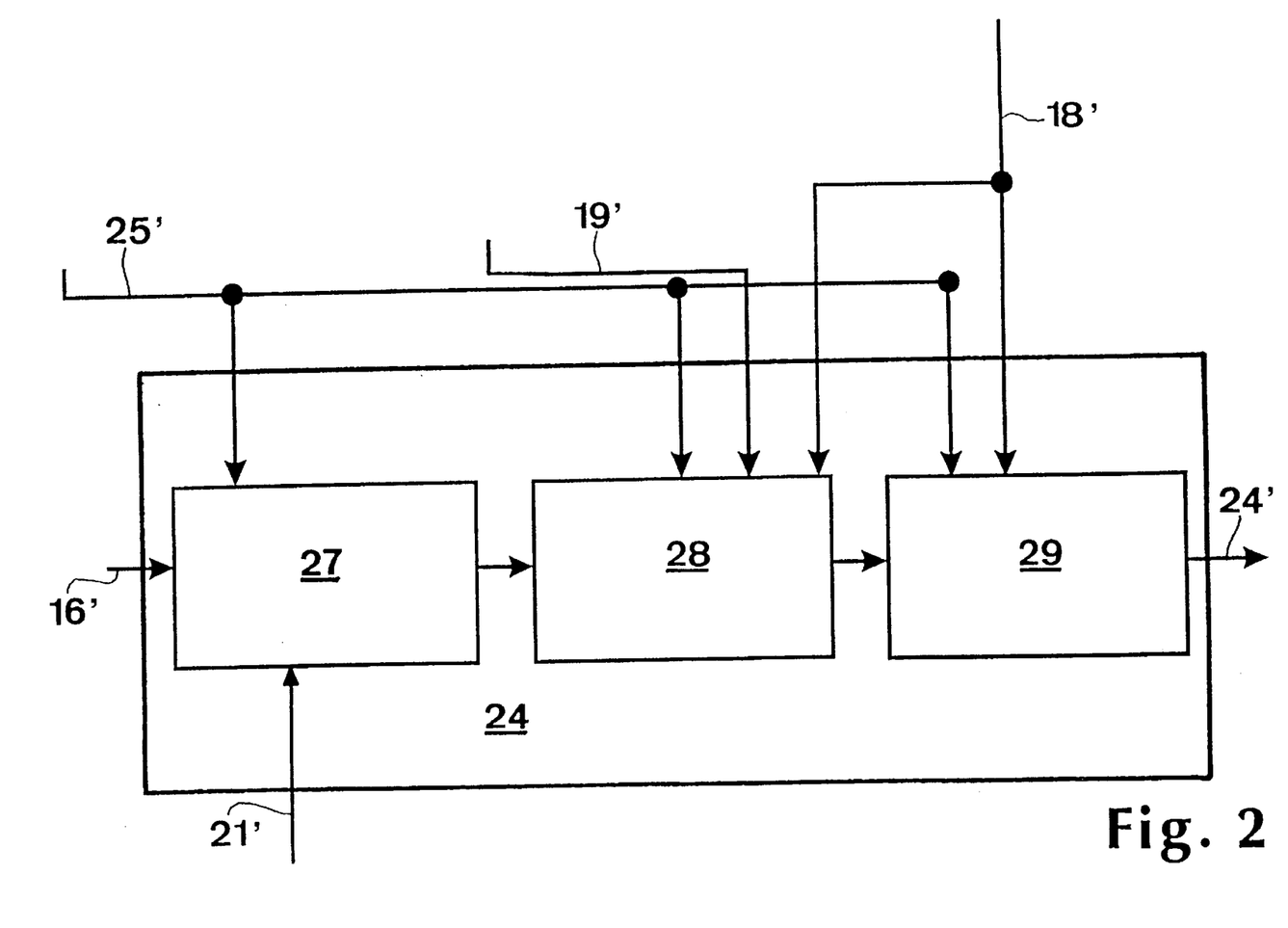
FIG. 2 is a block diagram of the structure of a unit for compensating for movement of the eye reference point of FIG. 1.

FIG. 2 depicts, in a block diagram, the eye reference point movement compensation unit 24 of FIG. 1 which is provided with a rotation compensation member 27, a scaling member 28 and a translation member 29. The rotation compensation member 27 is connected to the gaze direction line 16', the tracking value line 21' and the image screen coordinate line 25'. The gaze direction function values may be transformed into a moveable head coordinate system fixed on the head, by the rotation compensation member 27 by means of a rotation matrix which contains, as subject coordinate values, the tilt angle value and the pivot angle value of the gaze direction detector 9 as well as spatial coordinate values of the image screen 1.

The scaling member 28 at the output of the rotation compensation member 27 is connected to the spatial eye reference point line 18', the gaze direction detector line 19' and the image screen coordinate line 25'. Taking into consideration the fact that the image of the gaze direction function on the gaze direction detector is proportional to the distance between the eye 5 and the gaze direction detector 9 and that the image on the image screen 1 is proportional to the distance between the eye 5 and the image screen 1, the gaze direction function values in the head coordinate system may be multiplied by a scaling factor for defining the size of the image of the gaze direction function values on the image screen 1.

Finally, the translation compensation member 29 at the output of the scaling member 28 is connected to the spatial eye reference point line 18' as well as to the image screen coordinate line 25' and is set up for shifting the coordinate origin of the head coordinate system to the origin of the display coordinate system. The fixation point coordinates in the display coordinate system defined in this manner may be fed to the fixation point coordinate evaluation unit 26 through the fixation point line 24'.

Figure 3:
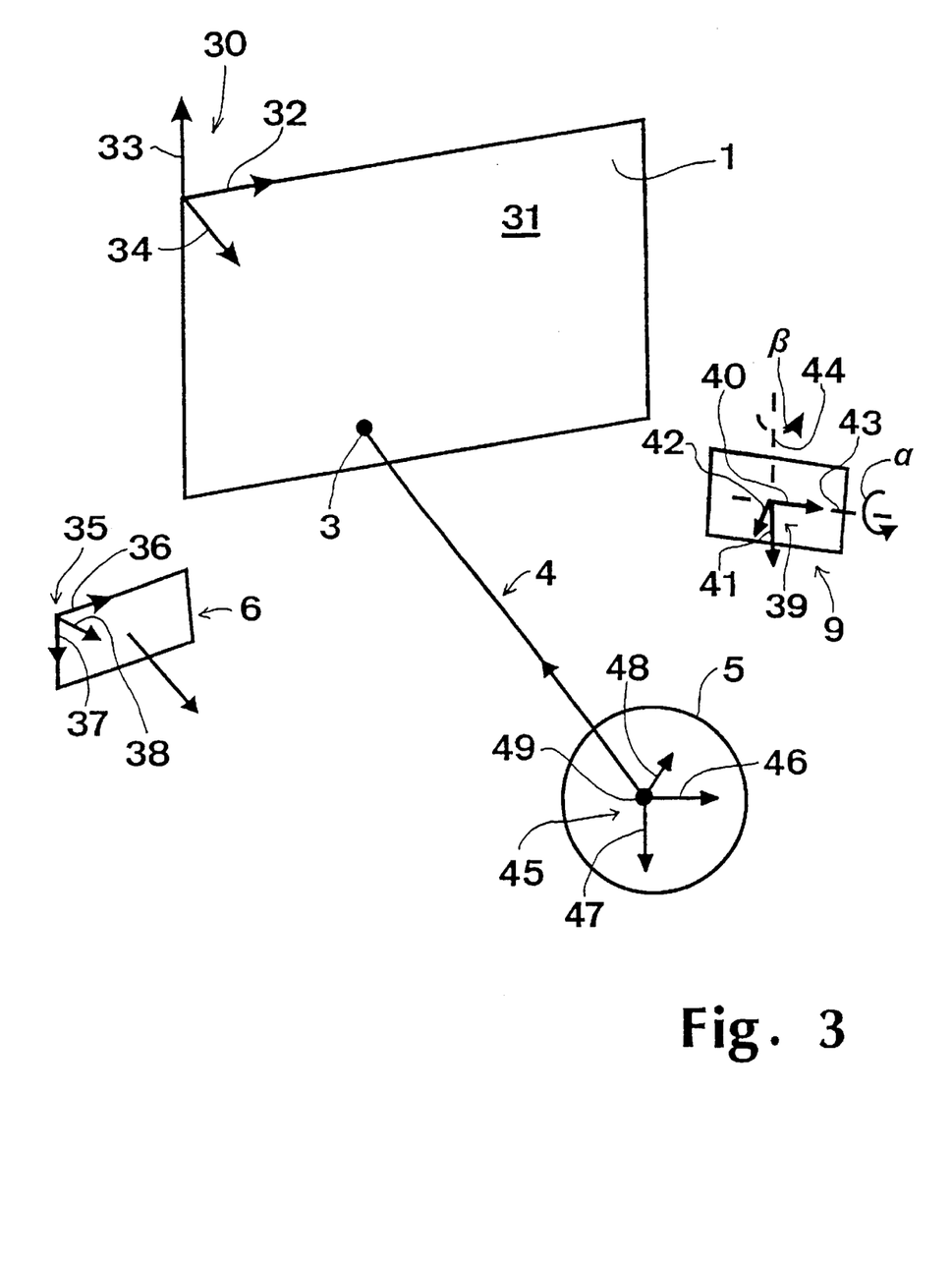
FIG. 3 is a schematic presentation of the coordinate systems used in the apparatus of FIG. 1.

FIG. 3 is a schematic presentation of the coordinate systems which are relevant to the apparatus in accordance with the invention. For instance, in the presentation of FIG. 3, the origin of a display coordinate system 30 associated with the image screen 1 is in the left upper corner of the image screen 1. If the image screen 1 is arranged spatially stationary, it is efficacious to select the display coordinate system 30 as a global coordinate system. The display surface 31 impinged by the line of view 4 is disposed in the $x_D$-$y_D$ plane defined by the $x_D$-axis 32 and the $y_D$-axis of the display coordinate system 30. A $z_D$-axis of the display coordinate system 30 is directed towards the eye 5. In a display coordinate system selected in this manner, the fixation point 3 on the surface 31 of the display has the coordinates $d_D=(d_{DX},d_{DY},0)$.

An eye reference point coordinate system 35 the $x_P$-axis 36 and $y_P$-axis 37 of which lie in the detector plane of the eye reference point detector 6, is associated with the eye reference point detector 6. The $z_P$-axis 38 of the eye reference point coordinate system 35 extends at a right angle from the $x_P$-axis 36 and $y_P$-axis 37.

Associated with the gaze direction detector 9, there is gaze direction coordinate system 39 the $x_B$-axis 41 as well as $Y_B$-axis of which lie in the detector plane of the gaze direction detector 9 and the $z_B$-axis of which is aligned with eye reference point which for reasons of measuring technology is preferably formed by the center of the pupil but which, in view of the precision, is ideally formed by the center of the eye.

The origin of the eye reference point coordinate system 35 in coordinates of the display coordinate system 30 lies in point $p_D=(p_{DX},p_{DY},p_{DZ})$. The origin of the gaze direction coordinate system 39 in the coordinates of the display coordinate system lies in point $b_D=(b_{DX},b_{DY},b_{DZ})$.

The gaze direction coordinate system 39 may be aligned with respect to the display coordinate system about a tilting axis 43 by a tilting angle α and about a pivot axis 44 by a pivot angle β.

In addition, a moveable head-mounted head coordinate system 45 is being introduced the origin of which lies in the eye reference point. The origin of the head coordinate system 45 has the coordinates $a_D=(a_{DX},a_{DY},aDZ)$ within the display coordinate system 30. An $x_K$-$y_K$-plane of the head coordinate system 45 defined by an $x_K$-axis 46 and $y_K$-axis 47 is aligned in parallel to the detector plane defined by the $x_B$-axis 40 and the $y_B$-axis 41 of the gaze direction coordinate system 39, whilst a $z_K$-axis 48 of the head coordinate system 45 is aligned parallel to the $z_B$-axis 42 of the gaze direction coordinate system 39.

Figure 4:
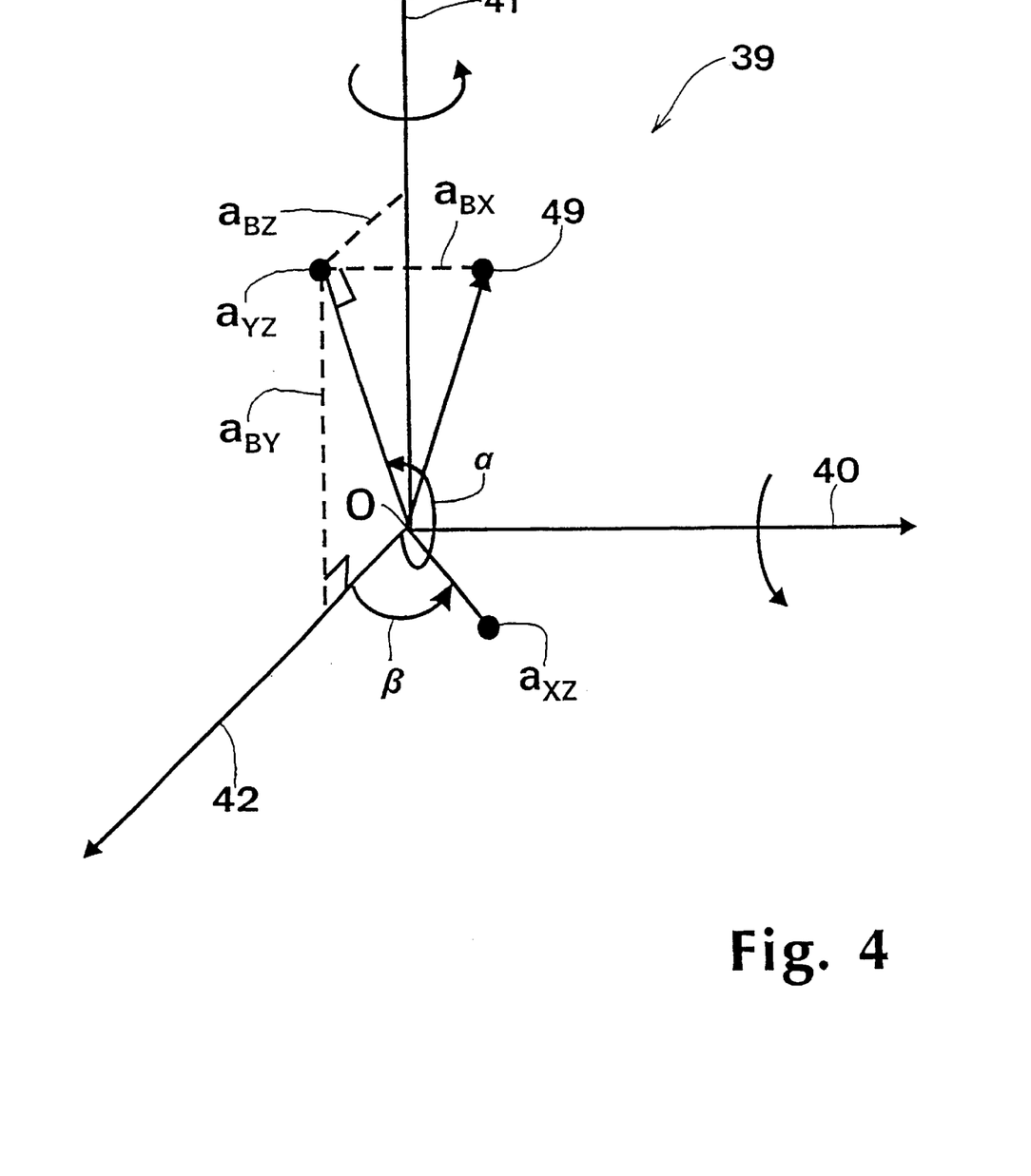
FIG. 4 is a graphic presentation of an alignment process of a gaze direction detection device of the embodiment of FIG. 1.

FIG. 4 is a graph of a tracking movement of the gaze direction detector 9 when moving the eye reference point 49 with the coordinates $a_B=(a_{BX},a_{BY},a_{BZ})$ in the gaze direction coordinate system 39 after tilting about the tilting angle α and pivoting about the pivot angle β in concert with the shift paths $a_{BX}$, $a_{BY}$, and $a_{BZ}$. When tilting about the tilting angle α the $x_B$-axis is rotated such that the $z_B$-axis lies on the path $Oa_{yz}$. When pivoting about the pivot angle β the gaze direction coordinate system is rotated about the $y_B$-axis 41 such that the $z_B$-axis 41 lies on the path between the origin O of the gaze direction coordinate system 39 and the eye reference point 49. The tilting angle then equals:

$$\alpha = -\arctan\frac{a_{BY}}{a_{BZ}} \quad (1)$$

and the pivot angle β equals:

$$\beta = \arctan\frac{a_{BX}}{\sqrt{a_{BY}2 + a_{BZ}2}} \quad (2)$$

For defining the coordinates of the fixation point 3 within the display coordinate system 39, it is necessary to transform the gaze direction function $f_B(g)=(f_{BX}(g_{BX},g_{BY}),F_{BY}(g_{BX},g_{BY}),a_{BZ})$ measured in the gaze direction coordinate system into the display coordinate system 30, wherein $g_{BX}$, $g_{BY}$ are the measuring values defining the view line of the gaze direction function $f_B(g)$, $f_{BX}$ and $f_{BY}$ are the components of the gaze direction function in the plane defined by the $x_B$-axis 40 and the $y_B$-axis, and $a_{BZ}$ is the distance between the eye reference point 49 and the $x_B$-$y_B$-plane 50.

Figure 5:
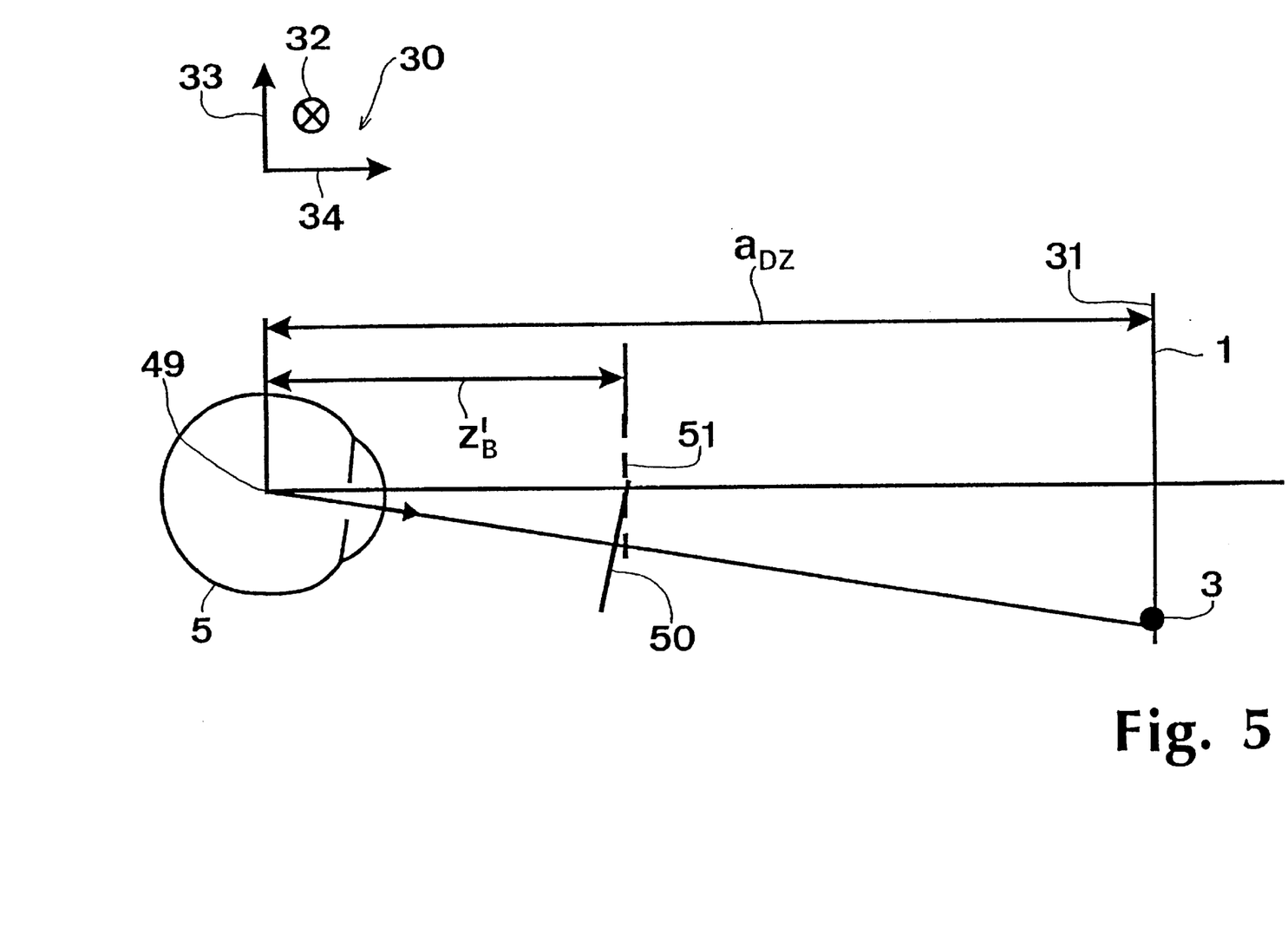
FIG. 5 is a graphic presentation of the operation of partial steps of compensation steps performed in the unit for compensating for movements of the eye reference point shown in FIG. 2.

FIG. 5 is a schematic presentation of the transformation process for transforming the gaze direction function $f_B(g)$ from the gaze direction coordinate system 39 to the display coordinate system of the image screen 1.

At the beginning of this transformation the gaze direction function $f_B(g)$ determined by the gaze direction detection device is known from its components $f_{BX}$, $f_{BY}$ and the distance $a_{BZ}$ which can be determined by the spatial eye reference point determining unit 18, the spatial coordinates $a_D=(a_{DX},a_{DY},a_{DZ})$ in the display coordinate system 30 determined by the eye reference point detection device as well as from the tilt angle α and the pivot angle β of the gaze direction detector 9.

In a first transformation step the gaze direction coordinate system 49 is rotated backwards by the angles -β, -α so that the $x_B$-$y_B$-plane 50 of the gaze direction detector 9 and the $x_D$-$y_D$-plane 50 formed by the $x_D$-axis 32 and the $y_D$-axis 33 and located in the display surface 31 are disposed parallel to each other. This rotation transformation is performed with the rotation compensation member 27 of the eye reference point movement compensation unit 24 of FIG. 1 and FIG. 2.

The resultant gaze direction function $f_B(g)$ is represented by $$f_B(g)=(f'_{BX},f'_{BY},z'_B)=R \cdot f_B(g), \quad (3)$$

wherein R is a rotation matrix and $f_B(g)$ is the gaze direction function measured in the gaze direction coordinate system 39.

At coincidence of the display coordinate system 30 and the global coordinate system, as is the case, for instance, with a stationary image screen 1, the rotation matrix R will be as follows:

$$R = R(-)R(-) = \begin{pmatrix} \cos & 0 & \sin \\ \sin\sin & \cos & -\sin\cos \\ -\cos\sin & \sin & \cos\cos \end{pmatrix} \quad (4)$$

wherein the angles α and β correspond to the angles of equations (1) and (2) supra.

This transformation is represented as a transposition of the $x_B$-$y_B$-plane 50 to the plane $x'_B$-$y'_B$-plane 51 disposed parallel to the display surface 31 according to FIG. 5.

In a second transformation step the gaze direction function $f_B(g)$ is scaled by the factor $$F = \frac{a_{DZ}}{z_B} \quad (5)$$

wherein $a_{DZ}$ is the distance between the eye reference point 49 and the display surface 31 and $z'_B$ is the distance between the eye reference point 49 and th $x'_B$-$y'_B$-plane 51 of FIG. 5. The value $z'_B$ is calculated as:

$$z'_B=(R \cdot f_B(g))_z \quad (6)$$

so that the gaze direction function on the image screen surface 31 now is:

$$(f'_B)_{XY}=F(R \cdot f_B(g))_{XY} \quad (7)$$

The transformation in accordance with equation (7) is performed with the scaling member 28.

In a third transformation step which may be performed with the translation compensation member 29, the origin of the head coordinate system 45 is shifted to the origin of the display coordinate system 30. The coordinates of the fixation point 3 in the display coordinate system 30 will thus be:

$$d_D = \begin{pmatrix} d_{DX} \\ d_{DY} \\ d_{DZ} \end{pmatrix} = \begin{pmatrix} f_{DX} \\ f_{DY} \\ z_D \end{pmatrix} = \begin{pmatrix} F(R \cdot f_B g))_X \\ F(R \cdot f_B g))_X \\ -a_{DZ} \end{pmatrix} = \begin{pmatrix} a_{DX} \\ a_{DY} \\ a_{DZ} \end{pmatrix} \quad (8)$$

An efficient transformation of relatively low mathematical complexity is achieved by the three transformation steps, i.e. rotation, scaling and translation of the x-y-components of the gaze direction function. As the rotation matrix R describes the actual angles of rotation α, β of the gaze direction detector 9 their mechanically precise monitoring is possible in a relatively simple way.

Any deviations of the actual angles of rotation α, β from the desired angles monitored by the spatial eye reference point determination unit 18 may be substantially reduced by feed-back of the eye reference point coordinate from the spatial eye reference point determination unit 18 to the tracking unit 21.

In many cases movement of the eye reference point 49 towards the gaze direction detector 9 and/or the image screen 1 substantially smaller than the distances $z_B$ and $a_{DZ}$ so that the scaling factor F is largely independent from the measuring precision of the eye reference point detector 6. The accuracy of the three transformation steps is substantially defined by the accuracy of the x-y-component of the eye reference point in the display coordinate system 30. These components are as a rule more accurate than the z-component.

Figure 6:
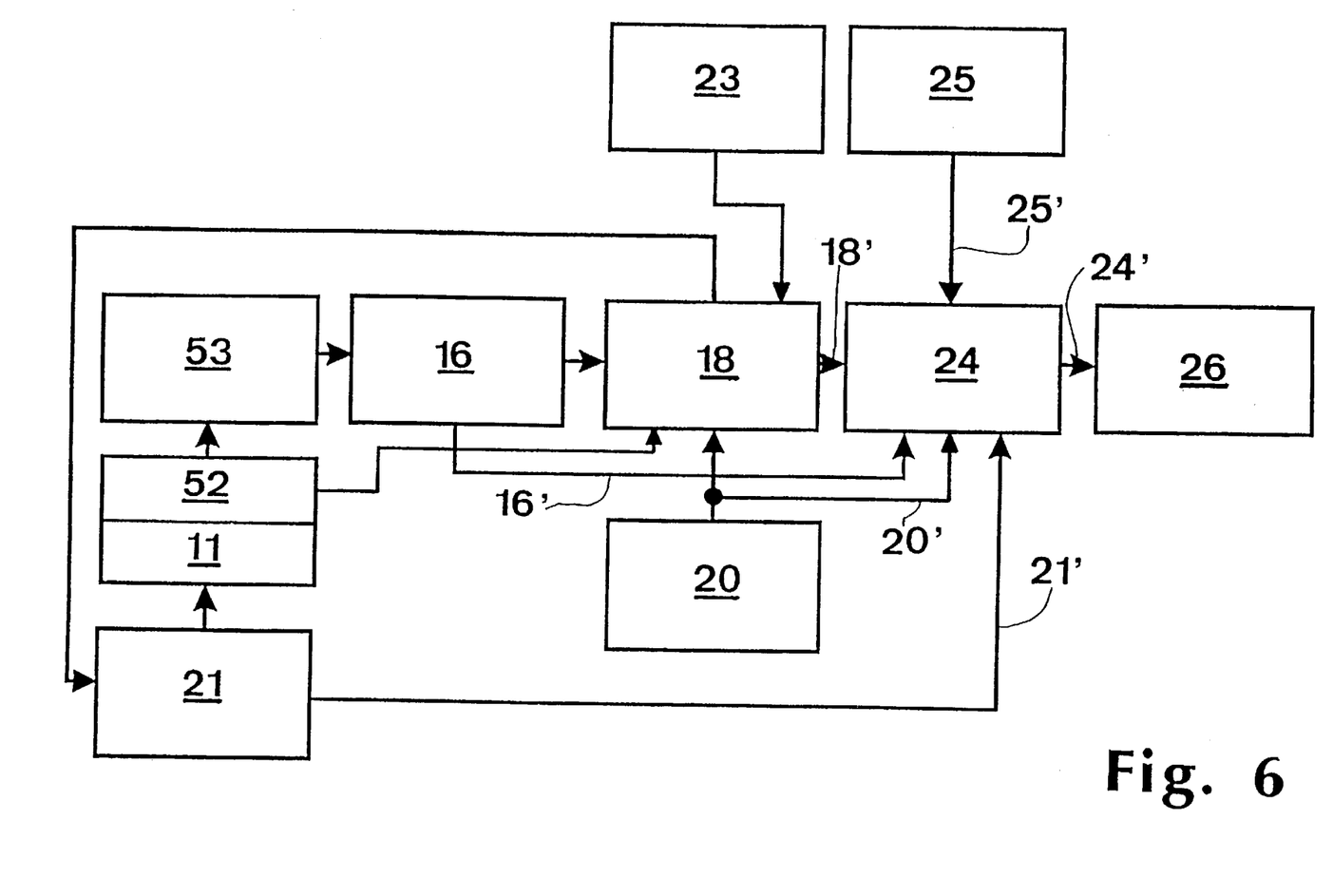
FIG. 6 is a block diagram of a further embodiment of an apparatus in accordance with the invention in which the eye reference point detection device and the gaze direction detection device are provided with a common pivotally and tiltably mounted surface detector.

FIG. 6 is a block diagram of a further embodiment of an apparatus in accordance with the invention wherein like structural components are shown with like reference characters and will hereinafter not be described in detail. The embodiment of FIG. 6, instead of the surface detector of the eye reference point detection device and the gaze direction detection device, there is provided with a common high-resolution dual detector 52 which is pivotally and titably mounted on the pivot and tilt platform 11 and provided with a autofocus module the autofocus values of which may be fed to the spatial eye reference point determination unit 18.

The image data storable in a dual image storage 53 and corresponding, for instance, to the image section of the gaze direction detector 9 of FIG. 1 may be fed to the surface gaze direction determination unit 16 as well as to the spatial eye reference point determination unit 18. As a variation from the embodiment of FIG. 1, the eye reference point may be defined by the spatial eye reference point determination unit 18 of FIG. 6 by means of the parametric data of the gaze direction parameter storage 20 associated with image characteristics from the dual detector 52 as well as by the autofocus values. The embodiment of FIG. 6 is characterized by a relatively small investment in equipment as only one surface detector is provided for determining the eye reference point as well as for monitoring the gaze direction.

What is claimed is:

1. Apparatus for estimating a fixation point of an anthropomorphically constructed eye (5) when viewing an object (1) with an eye reference point detection device for defining spatial eye reference point coordinates of an eye reference point (49), with a gaze direction detection device for defining a viewing direction of the eye as a viewing direction function, and with a computer for defining the fixation point (3) of the eye (5) from the gaze direction function and the eye reference point coordinate values, characterized by the fact that the eye reference point detection device comprises an eye reference point detector (6) structured as a surface detector by which an image of the eye (5) may be formed within a predetermined spatial range, that the gaze direction detection device comprises a gaze direction detector (9) arranged on a pivot and tilt element (11) which is pivotable and tiltable in two overlapping directions, whereby images may be formed by the gaze direction detector (9) of at least the pupil (13) and the immediate vicinity (14, 15) of the pupil and the pivot and tilt element (11) is adjustable by a tracking unit (21) fed with control signals from the eye reference point detection device such that during spatial movements of the eye reference point (49) the gaze direction detector (9) remains fixed on the eye reference point (49), and that the computer comprises a compensation unit (24) for compensating for the movement of the eye reference point (49) to which may be fed object coordinate values associated with the object, gaze direction coordinate values associated with the gaze direction detector (9), alignment values associated with the alignment of the gaze direction detector (9) and eye reference point coordinate values for defining the fixation point (3).

2. Apparatus according to claim 1, characterized by the fact that the compensation unit (24) comprises a rotation compensation member (27), a scaling member (28) and translation compensation member (29), whereby the gaze direction function may be corrected by the alignment values by means of the rotation compensation member (27), the size of the rotationally corrected gaze direction function may be calculated by the scaling member (28) during viewing of the object (1) and the displacement of the eye reference point (49) relative to the origin of an object coordinate system (30) may be corrected by the translation compensation member (29).

3. Apparatus according to claim 2, characterized by the fact that storages (19, 20, 22, 23, 25) are connected to the eye reference point detection unit and the compensation unit (24) for storing internal instrumentation related parameters and coordinate values of the eye reference point detection device and the gaze direction detection device as functions of the object coordinate system (30).

4. Apparatus according to claim 3, characterized by the fact that the gaze direction detection device is arranged for determining the gaze direction function by the so-called "cornea-reflex" method.

5. Apparatus according to claim 4, characterized by the fact that the eye reference point detection device comprises a surface eye reference point defining unit (8) for defining from the image of the eye reference point detector (9) the eye reference point (49) in surface coordinates of an eye reference point coordinate system (35) and that there is provided a spatial eye reference point determining unit (18) connected to the surface eye reference point determination unit (8) which in addition to surface coordinates from the surface eye reference point defining unit (8) may be fed with surface coordinates in a gaze direction coordinate system (39) of the eye reference point detector (6) and of the gaze direction detector (9) as well as the alignment values.

6. Apparatus according to claim 4, characterized by the fact that the eye reference point detection device and the gaze direction detection device comprise a common surface detector (52) mounted on the pivot and tilt element (11) for monitoring the eye (5) within a predetermined spatial range.

* * * * *